(12) United States Patent
Kawashima et al.

(10) Patent No.: US 9,192,588 B2
(45) Date of Patent: Nov. 24, 2015

(54) METHOD FOR PRODUCING A ZEAXANTHIN-ENRICHED CHICKEN EGG

(75) Inventors: Yuki Kawashima, Tokyo (JP); Hidetada Nagai, Tokyo (JP); Michihisa Ikarashi, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 25 days.

(21) Appl. No.: 14/000,494

(22) PCT Filed: Feb. 17, 2012

(86) PCT No.: PCT/JP2012/053787
§ 371 (c)(1),
(2), (4) Date: Aug. 20, 2013

(87) PCT Pub. No.: WO2012/114998
PCT Pub. Date: Aug. 30, 2012

(65) Prior Publication Data
US 2013/0330298 A1    Dec. 12, 2013

(30) Foreign Application Priority Data
Feb. 23, 2011 (JP) ................................. 2011-037619

(51) Int. Cl.
| | | |
|---|---|---|
| *A61K 31/07* | (2006.01) | |
| *A61K 35/74* | (2015.01) | |
| *A61K 9/00* | (2006.01) | |
| *A23K 1/00* | (2006.01) | |
| *A23L 1/32* | (2006.01) | |
| *A23K 1/16* | (2006.01) | |
| *A23K 1/18* | (2006.01) | |

(52) U.S. Cl.
CPC ............... *A61K 31/07* (2013.01); *A23K 1/008* (2013.01); *A23K 1/009* (2013.01); *A23K 1/1606* (2013.01); *A23K 1/1826* (2013.01); *A23L 1/32* (2013.01); *A23L 1/3208* (2013.01); *A23L 1/3212* (2013.01); *A61K 9/0056* (2013.01); *A61K 35/74* (2013.01)

(58) Field of Classification Search
CPC ..... A61K 31/07; A61K 9/0056; A61K 35/74; A23L 1/32; A23L 1/3212; A23L 1/3208; A23K 1/008; A23K 1/009; A23K 1/1606; A23K 1/1826
USPC ............... 426/614, 2, 807; 514/725; 424/93.2
See application file for complete search history.

(56) References Cited

U.S. PATENT DOCUMENTS

| | | | | |
|---|---|---|---|---|
| 3,841,967 | A | * 10/1974 | Dasek et al. | ........... 435/67 |
| 3,951,742 | A | * 4/1976 | Shepherd et al. | ........... 435/67 |
| 3,951,743 | A | * 4/1976 | Shepherd et al. | ........... 435/67 |
| 5,382,714 | A | 1/1995 | Khachik | |
| 2007/0105189 | A1 | 5/2007 | Tsubokura et al. | |
| 2008/0293097 | A1 | * 11/2008 | Mohamed et al. | ........... 435/67 |
| 2010/0233320 | A1 | * 9/2010 | Sunvold et al. | ........... 426/62 |

FOREIGN PATENT DOCUMENTS

| | | |
|---|---|---|
| JP | 05-049497 A | 3/1993 |
| JP | 05-328978 A | 12/1993 |
| JP | 07-059558 A | 3/1995 |
| JP | 07-143864 A | 6/1995 |
| JP | 08-080164 A | 3/1996 |
| JP | 08-092205 A | 4/1996 |
| JP | 10-155430 A | 6/1998 |
| JP | 2005-87097 A | 4/2005 |
| JP | 2005-224157 A | 8/2005 |
| JP | 2005-348725 A | 12/2005 |
| JP | 2007-151475 A | 6/2007 |
| JP | 2008-022703 A | 2/2008 |
| JP | 2008-167665 | * 7/2008 |

OTHER PUBLICATIONS

English Translation for JP2005-087097 published Apr. 2005.*
Ma, et al., "Effects of lutein and zeaxanthin on aspects of eye health", J. Sci. Food. Agric., 2010, vol. 90, No. 1, pp. 2-12.
Stahl, W., "Macular carotenoids: Lutein and zeaxanthin", Dev. Ophthalmol., 2005, vol. 38, pp. 70-88.
Tsushima, M., et al., "Inhibitory effect of natural carotenoids on epstein-barr virus activation activity of a tumor promoter in raji cells. A screening study for anti-tumor promoters", Biol. Pharm. Bull., 1995, vol. 18, No. 2, pp. 227-233.
Sugiura, M., et al., "Synergistic interaction of cigarette smoking and alcohol drinking with serum carotenoid concentrations: findings from a middle-aged Japanese population", Br. J. Nutr., 2009, vol. 102, No. 8, pp. 1211-1219.
Paust, J. et al., "Recent progress in commercial retinoids and carotenoids", Pure Appl. Chem., 1991, vol. 63, No. 1, pp. 45-58.
"3) Zeaxanthin, $C_{40}H_{56}O_2$", Biochromes, 7th ed., Aug. 10, 1974, p. 21, Asakura Publishing, Co., Ltd., Tokyo, Japan.
Ninet, L. and Renaut, J., "Chapter 17: Carotenoids", Carotenoids, in Microbial Technology, New York: Academic Press, New York, US, 1979, 2nd ed., vol. 1, pp. 529-544.
Yokoyama and Miki, "Compoistion and presumed biosynthetic pathway of carotenoids in the astaxanthin-producing bacterium Agrobacterium aurantiacum", FEMS Microbiology Letters, 1995, vol. 128, pp. 139-144.
Berry, et al., "*Paracoccus zeaxanthinifaciens* sp. nov., a zeaxanthin-producing bacterium", International Journal of Systematic and Evolutionary Microbiology, 2003, vol. 53, pp. 231-238.

(Continued)

*Primary Examiner* — Anthony Weier
(74) *Attorney, Agent, or Firm* — Lucas & Mercanti LLP

(57) ABSTRACT

An object of the present invention is to provide zeaxanthin-enriched poultry eggs containing zeaxanthin at high concentrations. The present invention specifically relates to zeaxanthin-enriched poultry eggs obtained by feeding poultry with a poultry feedstuff containing zeaxanthin-producing bacteria.

1 Claim, 2 Drawing Sheets

(56) References Cited

OTHER PUBLICATIONS

Bone, R.A. et al., "Lutein and zeaxanthin dietary supplements raise macular pigment density and serum concentrations of these carotenoids in humans", J. Nutr., 2003, vol. 133, No. 4, pp. 992-998.

Schalch, W. et al., "Xanthophyll accumulation in the human retina during supplementation with lutein or zeaxanthin—the LUXEA (LUtein Xanthophyll Eye Accumulation) study", Arch. Biochem. Biophys., 2007, vol. 458, No. 2, pp. 128-135.

Vishwanathan, R. et al., "Consumption of 2 and 4 egg yolks/d for 5 wk increases macular pigment concentrations in older adults with low macular pigment taking cholesterol-loweing statins", Am. J. Clin. Nutr., 2009, vol. 90, No. 5, pp. 1272-1279.

Goodrow, E.F. et al., "Consumption of one egg per day increases serum lutein and zeaxanthin concentrations in older adults without altering serum lipid and lipoprotein cholesterol concentrations", J. Nutr., 2006, vol. 136, No. 10, pp. 2519-2524.

Wenzel, A.J. et al., "A 12-wk egg intervention increases serum zeaxanthin and macular pigment optical density in women", J. Nutr., 2006, vol. 136, No. 10, pp. 2568-2573.

Eisenreich, W., et al.: "Biosynthesis of zeaxanthin via mevalonate in *Paracoccus* species strain PTA-3335. A product-based retrobiosynthetic study.", J. Org. Chem., Feb. 8, 2002; 67(3):871-875.

\* cited by examiner

SEQUENCE LISTING

```
<160> NUMBER OF SEQ ID NOS: 1

<210> SEQ ID NO 1
<211> LENGTH: 1452
<212> TYPE: DNA
<213> ORGANISM: Paracoccus carotinifaciens
<220> FEATURE:
<221> NAME/KEY: misc_feature
<222> LOCATION: (1350)..(1350)
<223> OTHER INFORMATION: n is a, c, g, or t

<400> SEQUENCE: 1
agtttgatcc tggctcagaa cgaacgctgg cggcaggctt aacacatgca agtcgagcga      60
gaccttcggg tctagcggcg gacgggtgag taacgcgtgg gaacgtgccc ttctctacgg     120
```

```
aatagccccg ggaaactggg agtaataccg tatacgccct ttgggggaaa gatttatcgg      180
agaaggatcg gcccgcgttg gattaggtag ttggtggggt aatggcccac caagccgacg      240
atccatagct ggtttgagag gatgatcagc cacactggga ctgagacacg gcccagactc      300
ctacgggagg cagcagtggg gaatcttaga caatgggggc aaccctgatc tagccatgcc      360
gcgtgagtga tgaaggcctt agggttgtaa agctctttca gctgggaaga taatgacggt      420
accagcagaa gaagcccgg ctaactccgt gccagcagcc gcggtaatac ggagggggct       480
agcgttgttc ggaattactg ggcgtaaagc gcacgtaggc ggactggaaa gtcagaggtg      540
aaatcccagg gctcaacctt ggaactgcct ttgaaactat cagtctggag ttcgagagag      600
gtgagtggaa ttccgagtgt agaggtgaaa ttcgtagata ttcggaggaa caccagtggc      660
gaaggcggct cactggctcg atactgacgc tgaggtgcga aagcgtgggg agcaaacagg      720
attagatacc ctggtagtcc acgccgtaaa cgatgaatgc cagacgtcgg caagcatgct      780
tgtcggtgtc acacctaacg gattaagcat tccgcctggg gagtacggtc gcaagattaa      840
aactcaaagg aattgacggg ggcccgcaca agcggtggag catgtggttt aattcgaagc      900
aacgcgcaga accttaccaa cccttgacat ggcaggaccg ctggagagat tcagctttct      960
cgtaagagac ctgcacacag gtgctgcatg gctgtcgtca gctcgtgtcg tgagatgttc     1020
ggttaagtcc ggcaacgagc gcaacccacg tccctagttg ccagcaattc agttgggaac     1080
tctatggaaa ctgccgatga taagtcggag gaaggtgtgg atgacgtcaa gtcctcatgg     1140
gccttacggg ttgggctaca cacgtgctac aatggtggtg acagtgggtt aatccccaaa     1200
agccatctca gttcggattg tcctctgcaa ctcgagggca tgaagttgga atcgctagta     1260
atcgcggaac agcatgccgc ggtgaatacg ttcccgggcc ttgtacacac cgcccgtcac     1320
accatgggag ttggttctac ccgacgacgn tgcgctaacc ttcgggggc aggcggccac      1380 ggtaggatca gcgactgggg tgaagtcgta acaaggtagc cgtaggggaa cctgcggctg     1440
gatcacctcc tt                                                        1452
```

METHOD FOR PRODUCING A ZEAXANTHIN-ENRICHED CHICKEN EGG

CROSS-REFERENCE TO RELATED APPLICATIONS

This application is a 371 of PCT/JP2012/053787, filed Feb. 17, 2012, which claims the benefit of Japanese Patent Application No. 2011-037619, filed Feb. 23, 2011, the contents of each of which are incorporated herein by reference.

TECHNICAL FIELD

The present invention relates to a zeaxanthin-enriched poultry egg and a method for producing the same, for example.

BACKGROUND ART

Carotenoids are natural pigments useful as feed additives, food additives, drugs, and the like. Examples of carotenoids include zeaxanthin, β-carotene, β-cryptoxanthin, astaxanthin, canthaxanthin, lycopene, phoenicoxanthin, adonixanthin, echinenone, asteroidenone, and 3-hydroxyechinenone.

Among carotenoids, zeaxanthin is added to feedstuffs as a natural yellow pigment contained in various plants such as corn. Known applications thereof include the improvement of the color tone of the egg yolk, meat, epidermis of poultry such as chickens, and food colorants. Moreover, zeaxanthin has a strong anti-oxidizing effect, and thus it has been revealed to play an important role in human eye health (Non-Patent Document 1). There is a high level of zeaxanthin in the macular region (central part) of the retina. It is considered to exhibit functions for filtering harmful light such as ultraviolet rays and to exhibit the functions of an antioxidant.

Based on these physiological effects, zeaxanthin is considered to be involved in overall eye health and, in particular, the risk of eye diseases such as Age-related Macular Degeneration (AMD) (Non-Patent Document 2). Other effects thereof that have been reported are anti-tumor effects (Non-Patent Document 3). Hence, zeaxanthin is considered to be a promising material for health foods and drugs.

Zeaxanthin kinetics in the human body when it is used for such applications are examined as follows. It is said that a human incorporates zeaxanthin into the body via the intestinal tract after intake of zeaxanthin orally from material consumed during a diet. Human in vivo kinetics of zeaxanthin incorporated into the human body are mediated by blood. Actually, human blood already contains zeaxanthin from a normal diet (Non-Patent Document 4). Furthermore, many attempts to increase human blood zeaxanthin concentration have been reported to date. Possible zeaxanthin sources are plant-based zeaxanthin sources including vegetables such as spinach and corn and citrus fruits such as oranges, animal-based zeaxanthin sources including chicken egg yolk, or supplements containing zeaxanthin. Of these sources, the concentrations of plant-based zeaxanthin sources cannot be easily increased in an artificial manner. Hence, methods for increasing such zeaxanthin concentrations are classified roughly into the following two categories: methods for increasing the concentration of zeaxanthin in chicken eggs by incorporating a zeaxanthin source into feedstuffs for chickens and methods for increasing human blood zeaxanthin levels using supplements.

As methods for producing zeaxanthin, a chemical synthesis method that involves using as a raw material optically active hydroxy ketone obtained by asymmetric reduction of oxoisophorone (Non-Patent Document 5) and a method that involves extracting it from corn seeds (Non-Patent Document 6) are known, for example. Furthermore, a method that involves extracting zeaxanthin from marigold is also known (Patent Document 1), however, a major ingredient of marigold-derived carotenoid is lutein and the zeaxanthin content is low.

Moreover, known examples of microorganisms producing zeaxanthin include spirulina algae (Patent Document 2), microalgae of the genus *Nannochloris* (Patent Document 3), bacteria of the genus *Flexibacter* (Patent Document 4), bacteria of the genus *Alteromonas* (Patent Document 5), bacteria of the genus *Flavobacterium* (Non-Patent Document 7), and *Agrobacterium aurantiacum* bacteria (Non-Patent Document 8). Furthermore, from among bacteria of the genus *Paracoccus* known as carotenoid-producing bacteria, *Paracoccus zeaxanthinifaciens* ATCC 21588 strain (Non-Patent Document 9), a mutant strain of *Paracoccus carotinifaciens* E-396 bacterial strain (Patent Document 6), a mutant strain of A-581-1 bacterial strain of the genus *Paracoccus* (Patent Document 6), and a mutant strain of bacteria of the genus *Paracoccus* (Patent Document 7) are known to produce zeaxanthin, for example.

An example of administration of zeaxanthin as a supplement to a human is the use of such a supplement obtained from industrial culture of Flavobacteria (Non-Patent Document 10). In such a case, when 30 mg of the supplement was taken every day for 120 days, the initial blood zeaxanthin concentration of 0.086 μM increased to 0.48 μM. In this case, the proportion of the increase to the intake was 0.01 μM/(mg/Day) ("μM/(mg/Day)" refers to the increase in the blood zeaxanthin concentration (μM) divided by the zeaxanthin intake per day (mg/Day)). In an example of administration of chemically synthesized zeaxanthin to a human (Non-Patent Document 11), when 12.6 mg of chemically synthesized zeaxanthin was taken every day for 6 months, the initial blood zeaxanthin concentration of 0.04 μM increased to 0.85 μM. In this case, the proportion of the increase to the intake was 0.06 μM/(mg/Day). Subsequently, when zeaxanthin in an amount twice the amount of the initial dose was further taken for 6 months, blood zeaxanthin concentration increased to 1.09 μM. In this case, the proportion of the increase to the intake was 0.01 μM/(mg/Day).

In contrast to these cases of administration of the supplements, several cases of increases in human blood zeaxanthin concentrations upon consumption of chicken eggs have been reported. When 2 chicken eggs/day or 4 chicken eggs/day were consumed for 35 days (Non-Patent Document 12), while the blood zeaxanthin concentration before consumption was 0.03 μM, the concentration increased to 0.05 μM and 0.06 μM, respectively. In this case, the proportion of the increase to the consumption was 0.03 μM/(mg/Day). Moreover, when 1 chicken egg/day was consumed for 35 days (Non-Patent Document 13), while the blood concentration before consumption was 0.04 μM, the blood concentration after consumption was 0.06 μM, and the proportion of the increase to the consumption (intake) was 0.16 μM/(mg/Day). When 6 chicken eggs/week were consumed for 12 weeks (Non-Patent Document 14), while the blood concentration before consumption was 0.1 μM, the blood concentration after consumption was 0.15 μM, and the proportion of the increase to the consumption (intake) was 0.43 μM/(mg/Day).

Taken together, the intake of zeaxanthin can be relatively easily increased in the above examples involving supplements, and thus human blood zeaxanthin concentration can be increased (0.48 μM to 1.09 μM). However, the effect of the intake on blood zeaxanthin concentration is very low, so that high intake thereof is required. In general, the production cost for carotenoids is very high, and thus such low efficiency is problematic.

Meanwhile, the number of chicken eggs that can be consumed per day is no higher than 1 to 2 chicken eggs per day, because of concern about cholesterol and the like. Therefore, the human blood zeaxanthin concentration that can be expected therefrom is very low (0.06 µM to 0.15 µM). However, in view of efficiency, the efficiency in the case of chicken eggs is higher than that in the case of supplements. Therefore, if a large amount of zeaxanthin can be introduced into a chicken egg, human blood zeaxanthin concentration can be increased easily and effectively.

In the recent chicken egg market, apart from general eggs obtained by feeding chickens with general feedstuffs, high-value added special eggs can be obtained by feeding chickens with a feedstuff supplemented with a functional ingredient such as folic acid (Patent Document 8), vitamin E (Patent Document 9), linseed (Patent Document 10), or astaxanthin (Patent Document 11).

As methods for increasing zeaxanthin concentration in egg yolk with the use of a feedstuff containing zeaxanthin, a method that involves adding spirulina alga body to a feedstuff (Patent Document 2), a method that involves adding Chinese wolfberry fruit or an extract thereof to a feedstuff (Patent Document 12), and the like are known.

However, production of high-concentration zeaxanthin-enriched eggs by adding spirulina to a feedstuff is problematic in that a large amount of spirulina must be added, since the zeaxanthin concentration in the spirulina alga body is low (1.0 mg/g). It is desirable that the amount added be as low as possible in order to keep the nutritional balance in the feedstuff. When zeaxanthin concentration has been enriched using spirulina, the zeaxanthin concentration in chicken egg yolk has been no higher than 1.65 mg/100 g.

Meanwhile, the addition of Chinese wolfberry fruit to a feedstuff has drawbacks such that, in addition to low zeaxanthin concentration in Chinese wolfberry fruit (1.1 mg/100 g), stable supplies thereof are difficult to attain, since the growth thereof is affected by weather. Furthermore, the zeaxanthin concentration in chicken egg yolk with a zeaxanthin concentration enriched using Chinese wolfberry fruit has been no higher than 3.35 mg/100 g.

Therefore, the following methods have been required: a method for producing chicken eggs using a raw material having a high zeaxanthin concentration, which allows the amount of the raw material necessary to add to a feedstuff to be low, and enables enrichment of the zeaxanthin concentration in chicken egg yolk to 3.35 mg/100 g or more and a stable supply of chicken eggs; and a method for efficiently increasing the human blood zeaxanthin level using such chicken eggs.

Patent Documents

Patent Document 1: JP Patent Publication (Kokai) No. 08-092205 A (1996)
Patent Document 2: JP Patent Publication (Kokai) No. 10-155430 A (1998)
Patent Document 3: JP Patent Publication (Kokai) No. 07-59558 A (1995)
Patent Document 4: JP Patent Publication (Kokai) No. 05-328978 A (1993)
Patent Document 5: JP Patent Publication (Kokai) No. 05-49497 A (1993)
Patent Document 6: JP Patent Publication (Kokai) No. 2005-87097 A
Patent Document 7: JP Patent Publication (Kokai) No. 2007-151475 A
Patent Document 8: JP Patent Publication (Kokai) No. 2005-224157 A
Patent Document 9: JP Patent Publication (Kokai) No. 2005-348725 A
Patent Document 10: JP Patent Publication (Kokai) No. 08-80164 A (1996)
Patent Document 11: JP Patent Publication (Kokai) No. 07-143864 A (1995)
Patent Document 12: JP Patent Publication (Kokai) No. 2008-22703 A Non-Patent Documents Non-Patent Document 1: Ma L. and Lin X. M., "J. Sci. Food. Agric.," 2010, Vol. 90, No. 1, pp. 2-12
Non-Patent Document 2: Stahl W., "Dev. Ophthalmol.," 2005, Vol. 38, pp. 70-88
Non-Patent Document 3: Tsushima M. et al., "Biol. Pharm. Bull.," 1995, Vol. 18, No. 2, pp. 227-233
Non-Patent Document 4: Sugiura M. et al., "Br. J. Nutr.," 2009, Vol. 102, No. 8, pp. 1211-1219
Non-Patent Document 5: Paust J. et al., "Pure Appl. Chem.," 1991, Vol. 63, No. 1, pp. 45-58
Non-Patent Document 6: "Biochrome," 1974, Asakura Publishing, Co., Ltd.
Non-Patent Document 7: L. Ninet and J. Renaut, "Carotenoids, in Microbial Technology," New York: Academic Press, 1979, $2^{nd}$ ed., Vol. 1, pp. 529-544
Non-Patent Document 8: Akihiro Yokoyama and Wataru Miki, "FEMS Microbiology Letters," 1995, Vol. 128, pp. 139-144
Non-Patent Document 9: Alan Berry et al., "International Journal of Systematic and Evolutionary Microbiology," 2003, Vol. 53, pp. 231-238
Non-Patent Document 10: Bone R. A. et al., "J. Nutr.," 2003, Vol. 133, No. 4, pp. 992-998
Non-Patent Document 11: Schalch W. et al., "Arch. Biochem. Biophys.," 2007, Vol. 458, No. 2, pp. 128-135
Non-Patent Document 12: Vishwanathan R. et al., "Am. J. Clin. Nutr.," 2009, Vol. 90, No. 5, pp. 1272-1279
Non-Patent Document 13: Goodrow E. F. et al., "J. Nutr.," 2006, Vol. 136, No. 10, pp. 2519-2524
Non-Patent Document 14: Wenzel A. J. et al., "J. Nutr.," 2006, Vol. 136, No. 10, pp. 2568-2573

SUMMARY OF THE INVENTION

Problems to be Solved by the Invention

In view of the above-mentioned circumstances, an object of the present invention is to provide zeaxanthin-enriched eggs that can be stably produced and contain zeaxanthin at high concentrations.

Means for Solving the Problem

As a result of intensive studies to achieve the above object, the present inventors have found that poultry eggs containing zeaxanthin at high concentrations can be produced by adding zeaxanthin-producing bacteria into feedstuffs for poultry such as chickens, and thus have completed the present invention.

The present invention encompasses the following (1) to (16).

(1) A poultry egg containing zeaxanthin in yolk at 3.5 mg to 10 mg per 100 g of yolk.
(2) The poultry egg according to (1), wherein the poultry are chickens.
(3) A zeaxanthin-enriched poultry egg, which is obtained by feeding poultry with a poultry feedstuff containing zeaxanthin-producing bacteria.
(4) The zeaxanthin-enriched poultry egg according to (3), wherein the bacteria belong to the genus *Paracoccus*.
(5) The zeaxanthin-enriched poultry egg according to (3) or (4), wherein the amount of zeaxanthin in the feedstuff is 1 mg or more per 100 g of the feedstuff.
(6) The zeaxanthin-enriched poultry egg according to any one of (3) to (5), containing zeaxanthin in yolk at 1.5 mg to 10 mg per 100 g of yolk.
(7) The zeaxanthin-enriched poultry egg according to any one of (3) to (6), wherein the poultry are chickens.
(8) A method for producing a zeaxanthin-enriched poultry egg comprising a step of feeding poultry with a poultry feedstuff containing zeaxanthin-producing bacteria.
(9) The method according to (8), wherein the bacteria belong to the genus *Paracoccus*.
(10) The method according to (8) or (9), wherein the amount of zeaxanthin in the feedstuff is 1 mg or more per 100 g of the feedstuff.
(11) The method according to any one of (8) to (10), wherein the zeaxanthin-enriched poultry egg contains zeaxanthin in yolk at 1.5 mg to 10 mg per 100 g of yolk.
(12) The method according to any one of (8) to (11), wherein the poultry are chickens.
(13) A poultry feedstuff containing zeaxanthin-producing bacteria.
(14) The poultry feedstuff according to (13), wherein the bacteria belong to the genus *Paracoccus*.
(15) The poultry feedstuff according to (13) or (14), wherein the amount of zeaxanthin to be added is 1 mg or more per 100 g of the feedstuff.
(16) The poultry feedstuff according to any one of (13) to (15), wherein the poultry are chickens.

This description comprises the contents described in the description and/or drawings of Japanese Patent Application No. 2011-037619, from which the present application claims the priority.

Effects of the Invention

According to the present invention, zeaxanthin-enriched poultry eggs containing zeaxanthin at high concentrations can be produced. Moreover, human blood zeaxanthin concentrations can be effectively increased using the zeaxanthin-enriched poultry eggs.

EMBODIMENTS FOR CARRYING OUT THE INVENTION

Figure 1:
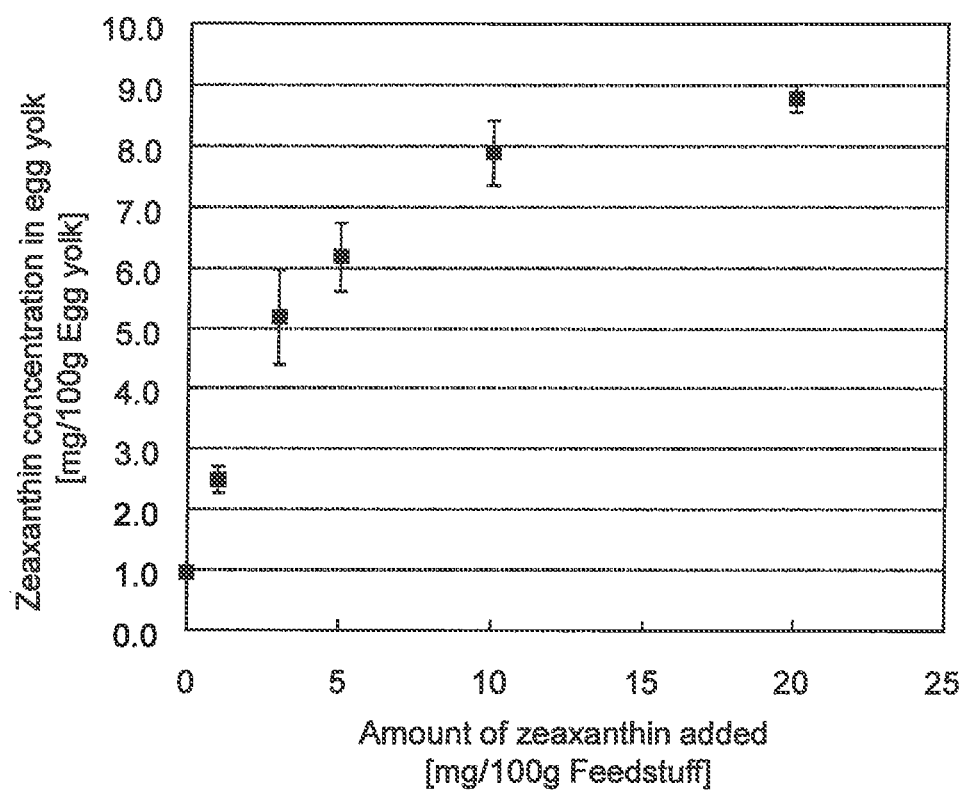
FIG. 1 is a graph showing zeaxanthin concentrations in zeaxanthin-enriched chicken egg yolk produced in Example 1.

Hereafter, the present invention is further described in detail. The scope of the present invention is not limited thereby. Regarding those other than the following examples, the present invention may be adequately changed without departing from the scope of the present invention.

The present invention relates to poultry eggs (hereinafter, may also be referred to as "zeaxanthin-enriched poultry egg(s)") containing zeaxanthin at high concentrations. The poultry eggs containing zeaxanthin at high concentrations can be obtained by adding zeaxanthin-producing bacteria to a poultry feedstuff, feeding poultry with the feedstuff, raising them, and then collecting eggs. Therefore, the present invention further relates to a method for producing zeaxanthin-enriched poultry eggs (hereinafter, referred to as "the method"), comprising a step of feeding poultry with a poultry feedstuff containing zeaxanthin-producing bacteria. According to the method, zeaxanthin can be contained at a high concentration in poultry egg yolk using zeaxanthin-producing bacteria.

Here, the term, "zeaxanthin-enriched poultry egg(s)" refers to poultry egg(s) in which zeaxanthin concentration in egg yolk is significantly higher than the same in general poultry egg yolk.

Examples of poultry include chickens, quails, turkeys, guinea fowls, pigeons, domestic ducks, and geese, and are particularly preferably chickens.

In the method, first, zeaxanthin-producing bacteria are prepared. Bacteria to be used in the method are not limited, as long as they produce zeaxanthin. Preferably, bacteria belonging to the genus *Paracoccus* are used. Among bacteria belonging to the genus *Paracoccus*, *Paracoccus carotinifaciens*, *Paracoccus marcusii*, *Paracoccus haeundaensis*, and *Paracoccus zeaxanthinifaciens* are preferably used and particularly *Paracoccus carotinifaciens* is preferably used. Examples of specific bacterial strains belonging to the genus *Paracoccus* include *Paracoccus carotinifaciens* E-396 strain (accession No. FERM BP-4283; International Authority Depository: the International Patent Organism Depositary, the National Institute of Advanced Industrial Science and Technology (Tsukuba Central 6, 1-1-1 Higashi, Tsukuba, Ibaraki, 305-8566, Japan); date of international deposit: Apr. 27, 1993), and bacteria of the genus *Paracoccus*, A-581-1 strain (accession No.: FERM BP-4671; International Authority Depository: the International Patent Organism Depositary, the National Institute of Advanced Industrial Science and Technology (Tsukuba Central 6, 1-1-1 Higashi, Tsukuba, Ibaraki, 305-8566, Japan); date of international deposit: May 20, 1994). Moreover, mutant strains prepared by mutating these strains to preferentially produce zeaxanthin compared with the parent strains are preferably used in the method. Moreover, another specific example of a strain of zeaxanthin-producing bacteria is *Paracoccus zeaxanthinifaciens* ATCC 21588 strain (Non-Patent Document 9).

Furthermore, bacteria to be used as zeaxanthin-producing bacteria have the nucleotide sequence of DNA preferably corresponding to 16S ribosomal RNA, which is substantially homologous to the nucleotide sequence shown in SEQ ID NO: 1 of the E-396 strain. Here, the expression "substantially homologous to" means that, in view of error frequency and the like upon determination of the nucleotide sequence of DNA, the nucleotide sequence have preferably 95% or more, more preferably 96% or more, further preferably 97% or more, particularly preferably 98% or more, and most preferably 99% or more homology therewith. Homology can be determined by gene analysis software, Clustal W, for example.

Moreover, the term "the nucleotide sequence of DNA corresponding to 16S ribosomal RNA" refers to a nucleotide sequence having a substitution of U (uracil) in the nucleotide sequence of 16S ribosomal RNA with T (thymine).

A method for culturing zeaxanthin-producing bacteria may be any method, as long as it is performed under conditions for producing zeaxanthin. For example, the method can be employed under the following conditions. Specifically, as a medium, a medium containing a carbon source, a nitrogen source, and an inorganic salt required for the growth of zeaxanthin-producing bacteria, and special substances required if necessary (e.g., vitamins, amino acids, and nucleic acids) is used.

Here, examples of a carbon source include: sugars such as glucose, sucrose, fructose, trehalose, mannose, mannitol, and maltose; organic acids such as acetic acid, fumaric acid, citric acid, propionic acid, malic acid, malonic acid; and alcohols such as ethanol, propanol, butanol, pentanol, hexanol, and isobutanol. One, two, or more types thereof are used. The amount thereof to be added herein differs depending on the type of carbon source, and generally ranges from 1 g to 100 g, and preferably from 2 g to 50 g per liter of medium.

Examples of a nitrogen source include potassium nitrate, ammonium nitrate, ammonium chloride, ammonium sulfate, ammonium phosphate, ammonia, and urea. One, two, or more types thereof are used. The amount thereof to be added differs depending on the type of a nitrogen source and generally ranges from 0.1 g to 20 g, and preferably 1 g to 10 g per liter of medium.

Examples of an inorganic salt include potassium dihydrogen phosphate, dipotassium hydrogen phosphate, disodium hydrogen phosphate, magnesium sulfate, magnesium chloride, ferric sulfate, ferric chloride, manganese sulfate, manganese chloride, zinc sulfate, zinc chloride, copper sulfate, calcium chloride, calcium carbonate, and sodium carbonate. One, two, or more types thereof are used. The amount thereof to be added differs depending the type of an inorganic salt and generally ranges from 0.1 mg to 10 g per liter of medium.

Furthermore, examples of a special substance required include vitamins, nucleic acids, yeast extracts, peptone, meat extracts, malt extracts, corn steep liquor, dry yeast, soybean cake, soybean oil, olive oil, corn oil, and flaxseed oil. One, two, or more types thereof are used. The amount thereof to be added differs depending on the type of a special substance required and generally ranges from 0.01 mg to 100 g per liter of medium.

The pH of a medium is adjusted to be pH 2 to 12 and preferably pH 6 to 9, for example.

Culture can be performed at a temperature between 10° C. and 70° C. and preferably between 20° C. and 35° C., for example, for generally 1 day to 20 days, and preferably 2 to 9 days by shaking culture or aeration-agitation culture.

Zeaxanthin-producing bacteria are cultured under the above-mentioned conditions. After culture, zeaxanthin-producing bacteria produce significant amounts of zeaxanthin within and outside the cells. Therefore, according to the present invention, a culture product (culture solution) can be directly added as zeaxanthin-producing bacteria to a poultry feedstuff.

Alternatively, a culture solution obtained by the above culture method is concentrated. Examples of a method for concentrating such a culture solution include membrane concentration and centrifugation. A more preferable example thereof is membrane concentration because of its cell separation performance. To improve cell separation performance, the pH of the relevant culture solution is adjusted to be 2 to 6. For pH adjustment, sulfuric acid is preferably used. Regarding concentration rate, it differs depending on the conditions of a culture solution, such as the pigment content, and preferably ranges from about 1.5-fold to 5-fold that of the relevant culture solution, for example.

Next, media components are removed. Upon centrifugation, water is added to the concentrate and then media components are removed. When membrane separation is employed, diafiltration is performed, and then media components are removed. The amount of water to be added differs depending on the conditions of the concentrate, such as pigment content, and is preferably about 1-fold to 5-fold that of the relevant concentrate, for example.

Moreover, a concentrate obtained by the above method is dried to produce a powder product. A drying method is not particularly limited. For example, known drying methods such as spray drying, spray granulation and drying, drum drying, lyophilization, and fluidized bed drying can be employed. As described above, zeaxanthin pigment-containing dry cells can be produced. The thus obtained dry cells can be added as zeaxanthin-producing bacteria to a poultry feedstuff. For example, 1 g of the dry cells of bacteria belonging to the genus *Paracoccus* contains a high content (about 1 mg to 20 mg and specifically, 1 mg/g to 20 mg/g) of zeaxanthin. Therefore, with the use of dry cells of bacteria belonging to the genus *Paracoccus* in the method, zeaxanthin concentrations in egg yolk obtained from poultry fed with the feedstuff can be increased even if the amount thereof added to the feedstuff is low.

According to the method, poultry are fed with a poultry feedstuff supplemented with zeaxanthin-producing bacteria such as zeaxanthin pigment-containing dry cells as the poultry are raised, and then eggs are collected from such poultry, thereby producing zeaxanthin-enriched poultry eggs. Zeaxanthin-producing bacteria are added to a poultry feedstuff so that 1 mg or more, such as 1 mg to 50 mg, and preferably 2 mg to 20 mg, of zeaxanthin (in zeaxanthin-producing bacteria) can be added per 100 g of the poultry feedstuff. For example, the above zeaxanthin pigment-containing dry cells are mixed with a poultry feedstuff that is generally used to raise poultry, such as in chicken farming. Zeaxanthin pigment-containing dry cell amount in a poultry feedstuff differs depending on zeaxanthin content in the dry cells, and preferably accounts for 0.05% by weight or more, and further preferably for 0.1% by weight to 5% by weight, of the poultry feedstuff.

Alternatively, zeaxanthin-producing bacteria such as zeaxanthin pigment-containing dry cells can be mixed with a poultry feedstuff and then the feedstuff can be administered to poultry. Moreover, zeaxanthin-producing bacteria can be mixed in advance with vitamins or the like in a premix and then poultry can be fed therewith.

Poultry fed with the poultry feedstuff containing zeaxanthin-producing bacteria such as zeaxanthin pigment-containing dry cells produce eggs rich in zeaxanthin (that is, zeaxanthin-enriched poultry eggs). According to the method, zeaxanthin-enriched poultry eggs containing zeaxanthin in yolk in an amount ranging from 1.5 mg to 10 mg (preferably, 3.5 mg to 10 mg, and particularly preferably 3.5 mg to 8 mg) per 100 g of egg yolk can be obtained, for example.

The above-explained zeaxanthin-enriched poultry eggs are consumed by humans, so that accumulation of zeaxanthin in human blood can be increased.

Accordingly, the present invention further relates to a method for increasing human blood zeaxanthin concentration, comprising causing humans to consume zeaxanthin-enriched poultry eggs. An increase in blood zeaxanthin concentration leads to prevention of diseases such as eye diseases (e.g., Age-related Macular Degeneration (AMD)). Zeaxanthin-enriched poultry eggs according to the present invention, which are used in this method, preferably contain 3.5 mg or more of zeaxanthin per 100 g of egg yolk, in order to efficiently increase human blood zeaxanthin concentration. Furthermore, consumption of one or more zeaxanthin-enriched poultry eggs per day can effectively increase the human blood zeaxanthin concentration. For example, if a human consumes such zeaxanthin-enriched poultry eggs in this manner, his or her human blood zeaxanthin concentration can be increased to 0.3 µM or more, with an efficiency of 0.28 µM/(mg/Day) or more.

Moreover, the present invention relates to the zeaxanthin-enriched poultry eggs to be used for increasing human blood zeaxanthin concentration, as well as the use of zeaxanthin-enriched poultry eggs for increasing human blood zeaxanthin concentration.

EXAMPLES

The present invention is explained in detail as follows using Examples, but the technical scope of the present invention is not limited to the Examples.

In addition, the quantitative determination of carotenoids in the Examples was performed as follows using high performance liquid chromatography (HPLC).

Two Inertsil SIL-100A 5-µm columns (φ4.6×250 mm) (GL Science) were connected and used. Elution was performed by applying a mobile-phase mixture of n-hexane, tetrahydrofuran, and methanol (40:20:1) at a constant temperature around room temperature at a flow rate of 1.0 mL per minute. Upon measurement, each sample was dissolved in tetrahydrofuran, the resultant was appropriately diluted with the mobile phase, 20 µL of the solution was injected, and a column eluate was detected at a wavelength of 470 nm. In addition, zeaxanthin (Cat. No. 0307 S, EXTRASYNTHESE) was used as a standard product for quantitative determination. Setting of a zeaxanthin concentration in a standard solution was performed by measuring absorbance (A) at 453 nm of the standard solution and peak area percentage % (B) of zeaxanthin when HPLC analysis had been conducted under the above conditions, and then using the following formula.

$$\text{Zeaxanthin concentration (mg/L)}=A \div 2327 \times B \times 100$$

Example 1

Production of Zeaxanthin-enriched Chicken Egg

The *Paracoccus carotinifaciens* E-396 strain (FERM BP-4283) was mutated with N-methyl-N'-nitro-N-nitrosoguanidine, and then yellow to orange colonies were selected. Carotenoid concentrations in culture solutions of the thus selected strains were measured, and then mutant strains having high capacity for producing zeaxanthin were selected.

A medium (2 L) with the following composition (sucrose (30 g/L), corn steep liquor (30 g/L), potassium dihydrogen phosphate (1.5 g/L), disodium hydrogen phosphate 12-hydrate (3.8 g/L), calcium chloride 2-hydrate (5.0 g/L), magnesium sulfate 7-hydrate (0.7 g/L), and ferric sulfate 7-hydrate (0.3 g/L), pH 7.2) was autoclaved at 121° C. for 20 minutes, so that a flask medium for seeding was prepared.

Next, a medium (40 L) with the following composition (glucose (30 g/L), corn steep liquor (30 g/L), ammonium sulfate (0.5 g/L), potassium dihydrogen phosphate (2.25 g/L), disodium hydrogen phosphate 12-hydrate (5.7 g/L), calcium chloride 2-hydrate (0.1 g/L), magnesium sulfate 7-hydrate (0.5 g/L), ferric sulfate 7-hydrate (5 g/L), sodium L-glutamate 1-hydrate (6 g/L), and alcohol-based antifoaming agent (0.5 g/L)) was added to a 100-L fermenter. Two such fermenters were prepared. D-biotin was added to each fermenter to 0.1 mg/L, followed by 30 minutes of autoclave sterilization at 121° C.

The above-selected zeaxanthin-producing bacterial strains belonging to the genus *Paracoccus* having high capacity for producing zeaxanthin were seeded in the above flask medium for seeding. After rotary shaking culture was performed at 27° C. for 2 days at 100 rpm, 2 L of the culture solution was seeded in each of the above fermenters, and then aerobic culture with a ventilation volume of 1 vvm was performed at 27° C. for 120 hours. The pH was continuously controlled with 15% ammonia water during culture so as to keep the pH at 7.2. Glucose was continuously supplied to prevent glucose depletion. The lowest figure for stirring rotations was 100 rpm, and the number of stirring rotations was varied so that the dissolved oxygen concentration in the culture solution during the mid-term of culture was maintained at 3 ppm. An alcohol-based antifoaming agent was automatically added to suppress foaming by sensing such foaming using a bubble sensor. The thus obtained culture solution was sterilized, cells were collected using a centrifuge, an appropriate volume of water was added to the thus obtained cells, and then the resultant was dried using a spray dryer.

Zeaxanthin pigment-containing dry cells were obtained from the culture solution by the above method. The zeaxanthin concentration in the zeaxanthin pigment-containing dry cells was 6.6 mg/g.

Subsequently, the thus obtained zeaxanthin pigment-containing dry cells were added to the basic feedstuff (layer S7, Chubu Shiryo Co., Ltd.), and then a feedstuff having a predetermined zeaxanthin concentration was prepared.

Laying hens to be fed with test feedstuffs were divided into 6 groups (with 3 laying hens per group). The zeaxanthin concentrations in the feedstuffs to be administered to the groups were zeaxanthin (0 mg/100 g for the group fed with a zeaxanthin-free feedstuff), zeaxanthin (1 mg/100 g for the group fed with a feedstuff supplemented with 1 mg/100 g zeaxanthin), zeaxanthin (3 mg/100 g for the group fed with a feedstuff supplemented with 3 mg/100 g zeaxanthin), zeaxanthin (5 mg/100 g for the group fed with a feedstuff supplemented with 5 mg/100 g zeaxanthin), zeaxanthin (10 mg/100 g for the group fed with a feedstuff supplemented with 10 mg/100 g zeaxanthin), and zeaxanthin (20 mg/100 g for the group fed with a feedstuff supplemented with 20 mg/100 g zeaxanthin). Laying hens were raised for 2 weeks. The amount of feedstuff was 50 g each in the morning and in the evening.

Eggs were collected from each test group. The amount of zeaxanthin in egg yolk of each of the thus obtained zeaxanthin-enriched chicken eggs was measured by high performance liquid chromatography. The results are shown in FIG. 1.

Example 2

Evaluation 1 of Blood Zeaxanthin Concentrations in Subjects Who Consumed Zeaxanthin-enriched Chicken Eggs Each subject consumed 5 soft-boiled zeaxanthin-enriched chicken eggs produced in Example 1 at once (zeaxanthin concentration in yolk: 3 mg/100 g) (corresponding to 2 eggs containing 7.5 mg/100 g zeaxanthin). After 24 hours, blood zeaxanthin concentration was measured. For a control group, each subject took 15 tablets of a zeaxanthin-containing supplement (1 tablet of spirulina-derived supplement having a zeaxanthin concentration of 0.17 mg per tablet). In a similar manner, after 24 hours, blood zeaxanthin concentration was measured. The results are shown in Table 1.

TABLE 1

|  | Zeaxanthin intake | Blood zeaxanthin concentration (μM) before consumption (intake) | Blood zeaxanthin concentration (μM) 24 h after consumption (intake) |
|---|---|---|---|
| Zeaxanthin-enriched chicken egg | 2.7 mg | 0.32 | 0.67 |
| Zeaxanthin supplement | 2.5 mg | 0.25 | 0.35 |

In the group that consumed zeaxanthin-enriched chicken eggs, blood zeaxanthin concentration roughly doubled. However, in the group that took the supplement, blood zeaxanthin concentration increased about 1.4-fold, indicating that zeaxanthin-enriched chicken eggs increased the blood zeaxanthin concentration more effectively.

Example 3

Figure 2:
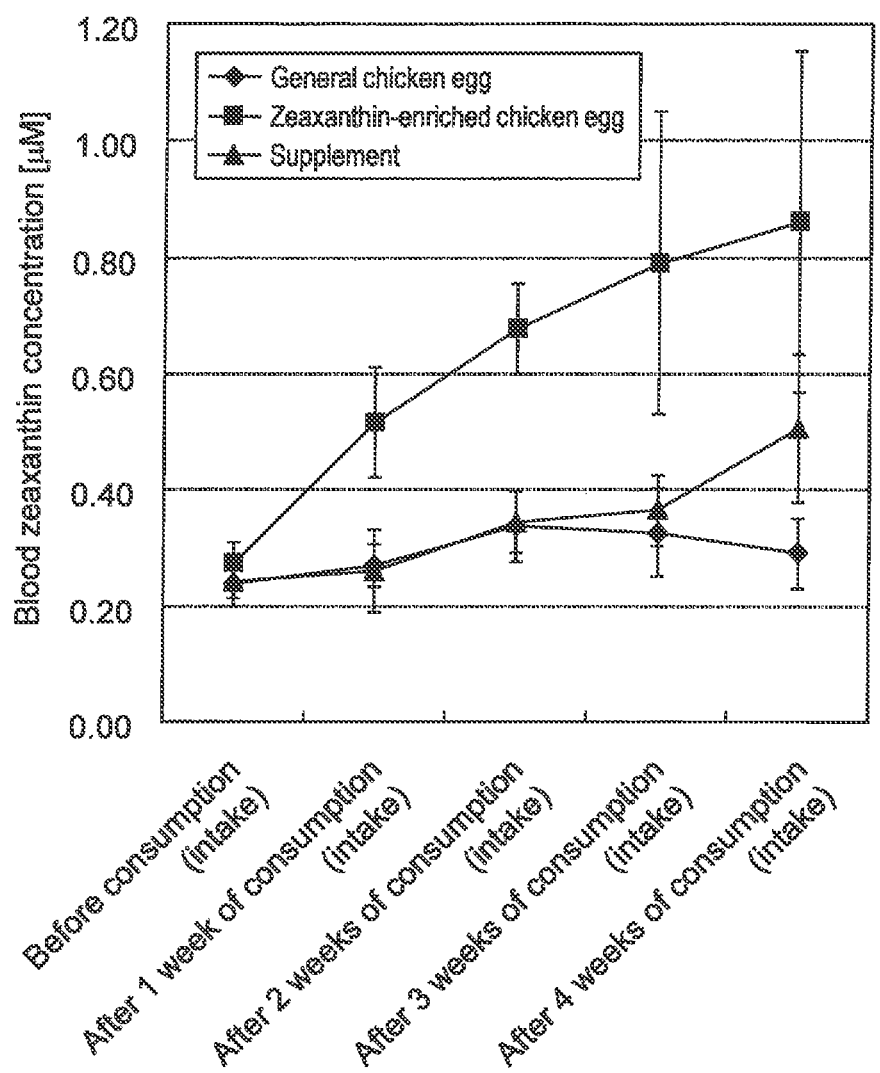
FIG. 2 is a graph showing blood zeaxanthin concentrations in subjects who consumed zeaxanthin-enriched chicken eggs in Example 3.

Evaluation 2 of Blood Zeaxanthin Concentrations in Subjects Who Consumed Zeaxanthin-enriched Chicken Eggs A total of 21 subjects were divided into 3 groups (7 subjects per group). The subjects in the groups continuously consumed: general chicken eggs (the group of subjects who consumed general chicken eggs with a zeaxanthin concentration (in yolk) of 1 mg/100 g), zeaxanthin-enriched chicken eggs (the group of subjects who consumed zeaxanthin-enriched chicken eggs with a zeaxanthin concentration (in yolk) of 4.5 mg/100 g); or a zeaxanthin supplement (the group of subjects who took spirulina-derived supplements with a zeaxanthin concentration (per tablet) of 0.17 mg/1 tablet) for 4 weeks. For the group of subjects who consumed general chicken eggs and the group of subjects who consumed zeaxanthin-enriched chicken eggs, each subject consumed 1 egg each after breakfast and after dinner (that is, 2 eggs per day). For the group of subjects who took the zeaxanthin supplement, each subject took 3 tablets of the supplement each after breakfast and dinner (that is, 6 tablets per day). The blood zeaxanthin concentration of each subject was measured every week. The analytical results are shown in Table 2 and FIG. 2.

TABLE 2

|  | Blood zeaxanthin concentration (μM) | | | | |
|---|---|---|---|---|---|
|  | Before consumption (intake) | After 1 week of consumption (intake) | After 2 weeks of consumption (intake) | After 3 weeks of consumption (intake) | After 4 weeks of consumption (intake) |
| General chicken egg | 0.24 ± 0.04 | 0.27 ± 0.04 | 0.34 ± 0.06 | 0.33 ± 0.08 | 0.29 ± 0.06 |
| Zeaxanthin-enriched chicken egg | 0.27 ± 0.04 | 0.52 ± 0.09 | 0.68 ± 0.08 | 0.79 ± 0.26 | 0.86 ± 0.29 |
| Supplement | 0.24 ± 0.03 | 0.26 ± 0.07 | 0.34 ± 0.05 | 0.37 ± 0.06 | 0.51 ± 0.13 |

It was successfully confirmed based on the above results that blood zeaxanthin concentrations significantly increased in the group of subjects who had consumed zeaxanthin-enriched chicken eggs, compared with the group of subjects who had consumed general chicken eggs and the group of subjects who had taken the supplement.

Accession Number

FERM BP-4283

FERM BP-4671

All publications, patents, and patent applications cited herein are incorporated herein by reference in their entirety.

The invention claimed is:

1. A method for producing a zeaxanthin-enriched chicken egg comprising:
   feeding chicken with a chicken feedstuff containing zeaxanthin-producing bacteria,
   wherein the egg contains zeaxanthin in yolk at 3.5 mg to 10 mg per 100 g of yolk,
   the bacteria belong to the genus *Paracoccus*, and
   the amount of zeaxanthin in the feedstuff is 2 mg to 5 mg per 100 g of the feedstuff.

* * * * *